United States Patent
Murai et al.

(10) Patent No.: US 9,724,642 B2
(45) Date of Patent: Aug. 8, 2017

(54) ACID GAS ABSORBENT, ACID GAS REMOVAL DEVICE, AND ACID GAS REMOVAL METHOD

(71) Applicant: Kabushiki Kaisha Toshiba, Minato-ku (JP)

(72) Inventors: Shinji Murai, Sagamihara (JP);
Yukishige Maezawa, Hachioji (JP);
Yasuhiro Kato, Kawasaki (JP);
Takehiko Muramatsu, Yokohama (JP);
Masatoshi Hodotsuka, Saitama (JP);
Satoshi Saito, Yamato (JP)

(73) Assignee: KABUSHIKI KAISHA TOSHIBA, Minato-ku (JP)

(*) Notice: Subject to any disclaimer, the term of this patent is extended or adjusted under 35 U.S.C. 154(b) by 102 days.

(21) Appl. No.: 14/555,787

(22) Filed: Nov. 28, 2014

(65) Prior Publication Data
US 2015/0151246 A1    Jun. 4, 2015

(30) Foreign Application Priority Data
Dec. 3, 2013    (JP) .................................. 2013-250241

(51) Int. Cl.
*C07C 217/28* (2006.01)
*C07C 217/08* (2006.01)
(Continued)

(52) U.S. Cl.
CPC ......... *B01D 53/62* (2013.01); *B01D 53/1475* (2013.01); *B01D 53/1493* (2013.01);
(Continued)

(58) Field of Classification Search
None
See application file for complete search history.

(56) References Cited

U.S. PATENT DOCUMENTS 3,478,096 A    11/1969 Cyba
4,112,052 A    9/1978 Sartori et al.
(Continued)

FOREIGN PATENT DOCUMENTS

CA    2 692 154       12/2008
CN    102553395 A     7/2012
(Continued)

OTHER PUBLICATIONS

Combined Office Action and Search Report issued Mar. 23, 2016 in Chinese Patent Application No. 201410725780.6 (with English translation of category of cited documents).
(Continued)

*Primary Examiner* — Daniel Berns
(74) *Attorney, Agent, or Firm* — Oblon, McClelland, Maier & Neustadt, L.L.P.

(57) ABSTRACT

An acid gas absorbent includes at least one kind of secondary amine compound represented by formula (1):

[General formula 1]

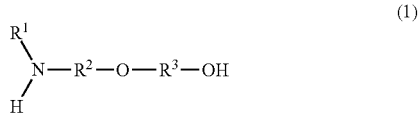

(1)

where $R^1$ is a cyclopentyl group or a cyclohexyl group which may be substituted by a substituted or non-substituted alkyl group having 1 to 3 carbon atoms, $R^2$ and $R^3$ each indicate an alkylene group having 2 to 4 carbon atoms, and $R^2$ and $R^3$ may each be the same or different, and be a straight chain or have a side chain.

14 Claims, 1 Drawing Sheet

(51) Int. Cl.
*C07C 217/52* (2006.01)
*C07C 215/42* (2006.01)
*B01D 53/62* (2006.01)
*B01D 53/14* (2006.01)

(52) U.S. Cl.
CPC .... *C07C 217/08* (2013.01); *B01D 2252/2023* (2013.01); *B01D 2252/20426* (2013.01); *B01D 2252/20484* (2013.01); *B01D 2252/502* (2013.01); *B01D 2252/602* (2013.01); *B01D 2252/606* (2013.01); *B01D 2252/608* (2013.01); *B01D 2257/304* (2013.01); *B01D 2257/504* (2013.01); *B01D 2258/0283* (2013.01); *Y02C 10/06* (2013.01)

(56) References Cited

U.S. PATENT DOCUMENTS

| | | | |
|---|---|---|---|
| 4,312,959 A * | 1/1982 | Treadwell | C07F 9/095 502/162 |
| 4,405,580 A | 9/1983 | Stogryn et al. | |
| 4,405,581 A | 9/1983 | Savage et al. | |
| 4,405,585 A | 9/1983 | Sartori et al. | |
| 4,405,811 A | 9/1983 | Stogryn et al. | |
| 4,471,138 A | 9/1984 | Stogryn | |
| 4,483,833 A | 11/1984 | Stogryn et al. | |
| 4,508,692 A | 4/1985 | Savage et al. | |
| 4,665,234 A | 5/1987 | Stogryn | |
| 5,413,627 A * | 5/1995 | Landeck | B01D 53/14 423/210 |
| 6,036,931 A | 3/2000 | Yoshida et al. | |
| 6,500,397 B1 | 12/2002 | Yoshida et al. | |
| 8,597,418 B2 | 12/2013 | Inoue et al. | |
| 2012/0161071 A1 | 6/2012 | Murai et al. | |
| 2013/0078170 A1 * | 3/2013 | Dai | B01F 17/0064 423/223 |
| 2014/0056792 A1 | 2/2014 | Inoue et al. | |

FOREIGN PATENT DOCUMENTS

| | | |
|---|---|---|
| EP | 0 084 943 A2 | 8/1983 |
| EP | 0 087 207 A1 | 8/1983 |
| EP | 0 087 208 A1 | 8/1983 |
| EP | 0 558 019 A2 | 9/1993 |
| EP | 2 189 207 A1 | 5/2010 |
| EP | 2 468 385 A2 | 6/2012 |
| GB | 1 238 696 A | 7/1971 |
| JP | 58-124520 | 7/1983 |
| JP | 63-27336 | 6/1988 |
| JP | 2871334 | 3/1999 |
| JP | 2008-307519 | 12/2008 |
| JP | 2009-006275 | 1/2009 |
| JP | 2009-213974 | 9/2009 |
| WO | WO 2008/156085 A1 | 12/2008 |

OTHER PUBLICATIONS

Extended European Search Report issued May 20, 2015 in Patent Application No. 14195550.0.

* cited by examiner

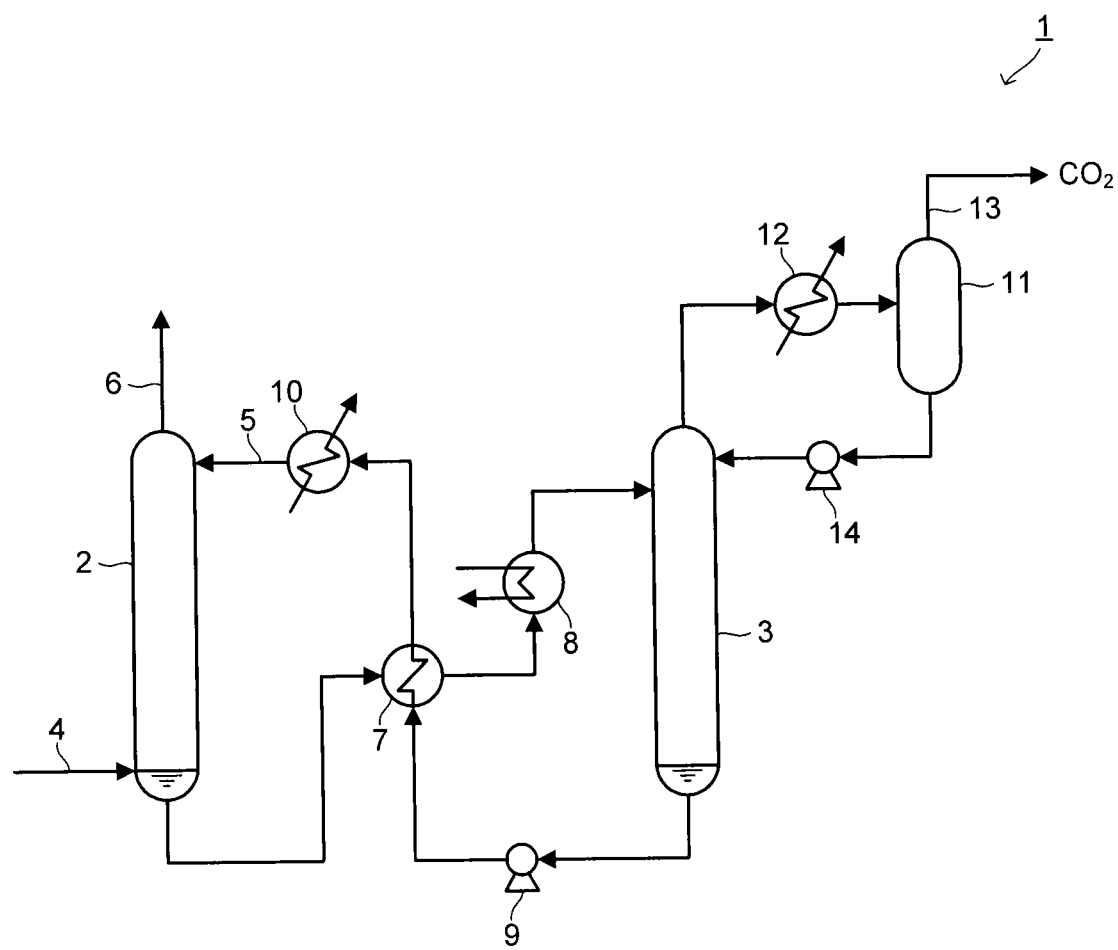

ACID GAS ABSORBENT, ACID GAS REMOVAL DEVICE, AND ACID GAS REMOVAL METHOD

CROSS-REFERENCE TO RELATED APPLICATION

This application is based upon and claims the benefit of priority from Japanese Patent Application No. 2013-250241, filed on Dec. 3, 2013; the entire contents of all of which are incorporated herein by reference.

FIELD

Embodiments described herein relate generally to an acid gas absorbent, an acid gas removal device, and an acid gas removal method.

BACKGROUND

In recent years, a greenhouse effect resulting from an increase in carbon dioxide ($CO_2$) concentration has been pointed out as a cause of global warming phenomena, and there is an urgent need to devise an international countermeasure to protect environment in a global scale. Industrial activities have a large responsibility as a generation source of $CO_2$, and there is a trend to suppress discharge of $CO_2$.

As technologies to suppress the increase of the concentration of acid gas, typically, $CO_2$, there are a development of energy saving products, technologies to use the acid gas as a resource and to isolate and store the acid gas, a switching to alternate energies such as natural energy, atomic energy, and so on which do not discharge the acid gas, and so on, and a separation and recovery technology of discharged acid gas is known as one of them.

As separation technologies of the acid gas that have been studied up to now, there are an absorption process, a suction process, a membrane separation process, a cryogenic process, and so on. Among them, the absorption process is suitable for processing a large amount of gas, and its application in a factory and a power station is considered.

Mainly, as a method whose targets are facilities such as a thermal power station using fossil fuels (coal, coal oil, natural gas, and so on), a method in which exhaust combustion gas generated when the fossil fuel is burned is brought into contact with a chemical absorbent, and thereby $CO_2$ in the exhaust combustion gas is removed and recovered, and further a method of storing the recovered $CO_2$ are known. Further, there is proposed to remove acid gas such as hydrogen sulfide ($H_2S$) in addition to $CO_2$ by using the chemical absorbent.

In general, alkanolamine typified by monoethanolamine (MEA) have been developed in the 1930s as the chemical absorbent used in the absorption process, and are still used at present. A method of using the alkanolamine is economical, and further it is easy to enlarge the removal device in size.

As alkanolamine used in the absorption process, there are monoethanolamine, 2-amino-2-methylpropanol, methylaminoethanol, ethylaminoethanol, propylaminoethanol, diethanolamine, methyldiethanolamine, dimethylethanolamine, diethylethanolamine, triethanolamine, dimethylamino-1-methylethanol, and so on.

In particular, monoethanolamine being primary amine has been widely used because its reaction speed is fast. However, there are problems that this compound has corrosiveness, is easily deteriorated, and requires high energy for regeneration. On the other hand, methyldiethanolamine being tertiary amine has low corrosiveness and requires low energy for regeneration, but has a defect that an absorption speed is low. Accordingly, a development of a new absorbent in which these disadvantages are improved is required. Besides, an amine compound which is difficult to be released from an absorption tower and a regeneration tower is required.

In recent years, a study on particularly alkanolamine having structural steric hindrance, among amine compound, has been tried as the absorbent of acid gas. Alkanolamine having the steric hindrance has advantages that selectivity of acid gas is very high and the energy required for regeneration is small.

The reaction speed of the amine compound having the steric hindrance depends on the degree of reaction hindrance determined by the steric structure thereof.

There is a method to use the alkanolamine which has both the ether bond and the chained alkyl group which is directly coupled to a nitrogen atom.

However, the alkanolamine suffers from the disadvantages of the latively low boiling point, the insufficient suppression of the diffusion from the absorption tower, and high heat of reaction with acid gas.

On the other hand, there is a method to use a cyclic amine compound which has a chemical structure different from that of alkanolamine.

BRIEF DESCRIPTION OF THE DRAWINGS

FIG. 1 is a schematic diagram of an acid gas removal device according to an embodiment.

DETAILED DESCRIPTION

Hereinafter, an embodiment of the present invention will be explained in detail. An acid gas absorbent according to an embodiment includes at least one kind of secondary amine compound represented by the following general formula (1).

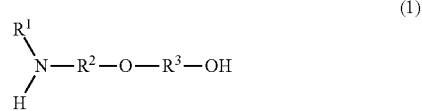

In the above-described formula (1), $R^1$ indicates a cyclopentyl group or a cyclohexyl group which may be substituted by a substituted or non-substituted alkyl group having 1 to 3 carbon atoms. $R^2$ and $R^3$ each indicate an alkylene group having 2 to 4 carbon atoms. $R^2$ and $R^3$ may each be the same or different, and be a straight chain or have a side chain.

Conventionally, it has been known that a steric hindrance held by an amine compound has a large effect on a product at a carbon dioxide absorption, and plays an advantageous role in generation of bicarbonate ion exhibiting low heat of reaction. As a result that based on such knowledge, the present inventor conducted studies to obtain a larger effect of the steric hindrance, it was found that it is possible to obtain further lower heat of reactivity, higher carbon dioxide absorption amount, further higher boiling point, and to suppress diffusion from an acid gas absorbent by using the compound represented by the above-described general formula (1) (for example, 2-[2-(cyclopentylamino)ethoxy]ethanol) than the conventional amine compound.

That is, the secondary amine compound represented by the above-described general formula (1) (hereinafter, referred to as a secondary amine compound (1)) has a structure in which a hydroxyl group is coupled to nitrogen atom of an amino group via an ether bond represented by $—R^2—O—R^3—$, and further a cyclic alkyl group is directly coupled to nitrogen atom of an amino group. The structure in which the hydroxyl group is coupled to the nitrogen atom via the ether bond enables to suppress the diffusion from the absorbent.

Besides, the secondary amine compound (1) in which the cyclic alkyl group is directly coupled to nitrogen atom of an amino group has a structure with a large steric hindrance. Accordingly, it has high reactivity for the acid gas such as carbon dioxide ($CO_2$), and it is possible to obtain high acid gas absorption amount.

As stated above, in the secondary amine compound (1), the alkyl group $R^1$ which directly couples to nitrogen atom of an amino group is forming a cyclic structure, and thereby, volatility is suppressed compared to a case when the alkyl group $R^1$ does not form the cyclic structure, namely, when $R^1$ is a chain alkyl group or a branched alkyl group. Accordingly, it is possible to enable the acid gas absorbent in which an amount of amine component to be released into the atmosphere in the course of processing the acid gas is reduced. Further, the alkyl group $R^1$ which is coupled to the nitrogen atom forms the cyclic structure, and thereby, the heat of reaction when the secondary amine compound (1) reacts with the acid gas is reduced.

The secondary amine compound (1) is dissolved in a solvent such as, for example, water, and thereby, an acid gas absorbent having high acid gas absorption capacities can be obtained. In the following embodiment, the case when the acid gas is carbon dioxide will be explained as an example, but the acid gas absorbent according to the embodiment of the present invention is able to exhibit similar effects for other acid gases such as hydrogen sulfide.

In the above-described formula (1), $R^1$ represents a cyclopentyl group or a cyclohexyl group. The cyclopentyl group or the cyclohexyl group may be substituted by the substituted or non-substituted alkyl group having 1 to 3 carbon atoms.

When $R^1$ has less than 5 carbon atoms in the formula (1), for example, in the secondary amine compound represented by the formula (1) but in which $R^1$ is a cyclopropyl group or a cyclobutyl group, the heat of reaction with the acid gas is not enough reduced. On the other hand, when $R^1$ has over 6 carbon atoms in the formula (1), for example, in the secondary amine compound represented by the formula (1) but in which $R^1$ is a cycloheptyl group, a recovery performance of the acid gas is lowered because solubility for a solvent such as water is lowered. $R^1$ is more preferably the cyclopentyl group.

In the above-described formula (1), $R^2$ and $R^3$ are each independently an alkylene group having 2 to 4 carbon atoms, and the alkylene group having 2 or 3 carbon atoms is preferable for both of them from the viewpoint of solubility. $R^2$ and $R^3$ may each be a straight chain or have a side chain. Besides, $R^2$ and $R^3$ may each be the same or different.

In the secondary amine compound represented by the formula (1) but in which $R^2$ and/or $R^3$ has one carbon atom, stability thereof is lowered. On the other hand, in the secondary amine compound represented by the formula (1) but in which $R^2$ and/or $R^3$ has 5 or more carbon atoms, solubility for the solvent such as water is lowered.

As $R^2$ and $R^3$, for example, an ethylene group, a propylene group, and a butylene group can be cited, and the ethylene group is more preferable for both of them.

As the secondary amine compound (1) in which the cyclic alkyl group is coupled to the nitrogen atom, the following compounds can be cited. Namely, as the secondary amine compound (1), there can be cited, 2-[2-(cyclopentylamino)ethoxy]ethanol, 2-[2-(cyclohexylamino)ethoxy]ethanol, 2-[3-(cyclopentylamino)propoxy]ethanol, 2-[3-(cyclohexylamino)propoxy]ethanol, 2-[4-(cyclopentylamino)butoxy]ethanol, 2-[4-(cyclohexylamino)butoxy]ethanol, 3-[2-(cyclopentylamino)ethoxy]-1-propanol, 3-[2-(cyclohexylamino)ethoxy]-1-propanol, 3-[3-(cyclopentylamino)propoxy]-1-propanol, 3-[3-(cyclohexylamino)propoxy]-1-propanol, 3-[4-(cyclopentylamino)butoxy]-1-propanol, 3-[4-(cyclohexylamino)butoxy]-1-propanol, 1-[2-(cyclopentylamino)ethoxy]-2-propanol, 1-[2-(cyclohexylamino)ethoxy]-2-propanol, 1-[3-(cyclopentylamino)propoxy]-2-propanol, 1-[3-(cyclohexylamino)propoxy]-2-propanol, 1-[4-(cyclopentylamino)butoxy]-2-propanol, 1-[4-(cyclohexylamino)butoxy]-2-propanol, 4-[2-(cyclopentylamino)ethoxy]-1-butanol, 4-[2-(cyclohexylamino)ethoxy]-1-butanol, 4-[3-(cyclopentylamino)propoxy]-1-butanol, 4-[3-(cyclohexylamino)propoxy]-1-butanol, 4-[4-(cyclopentylamino)butoxy]-1-butanol, 4-[4-(cyclohexylamino)butoxy]-1-butanol, and so on.

The acid gas absorbent absorbing $CO_2$ is regenerated by heating at a high-temperature range of approximately 120° C. Accordingly, it is preferable that the secondary amine compound (1) having the high boiling point is used as the secondary amine compound (1) which is difficult to be released from the regeneration tower when it is heated. Therefore, it is preferable to have an alkyl group having large number of carbon atoms as the secondary amine compound (1) from the viewpoint of suppressing the diffusion capability.

The boiling point of the secondary amine compound (1) is preferably 170° C. to 400° C., and more preferably 200° C. to 400° C.

Note that as the secondary amine compound (1), it is possible to use one kind of compound selected from the above-stated group, and it is also possible to use one in which two or more kinds of compounds selected from the above-stated group are mixed.

A content of the secondary amine compound (1) contained in the acid gas absorbent is preferably 10 mass % to 55 mass %. In general, an absorption amount and a desorption amount of carbon dioxide per unit capacity are larger and an absorption speed and a desorption speed of carbon dioxide are faster as a concentration of the amine component in the acid gas absorbent is higher, and thus, this is preferable in view of energy consumption, a size of a plant facility, and process efficiency. However, it becomes impossible for the water contained in the acid gas absorbent to fully exhibit a function as an activator for the absorption of carbon dioxide when the concentration of the amine component in the acid gas absorbent is too high. Further, defects such as an increase in viscosity of the acid gas absorbent become not negligible when the concentration of the amine component in the acid gas absorbent is too high.

When the content of the secondary amine compound (1) is 55 mass % or less, phenomena such as the increase in viscosity of the acid gas absorbent and the deterioration of the function of water as the activator are not recognized.

Further, by setting the content of the secondary amine compound (1) to 10 mass % or more, it is possible to obtain sufficient absorption amount and absorption speed of carbon dioxide, and to obtain excellent process efficiency.

When the acid gas absorbent having the content of the secondary amine compound (1) within the range of 10 mass % to 55 mass % is used for recovery of carbon dioxide, not only the carbon dioxide absorption amount and the carbon dioxide absorption speed are high but also the carbon dioxide desorption amount and the carbon dioxide desorption speed are high. Therefore, it is advantageous in that the recovery of carbon dioxide can be performed efficiently. The content of the secondary amine compound (1) is more preferably 20 mass % to 50 mass %.

The secondary amine compound (1) is preferably used while being mixed with a reaction accelerator composed of alkanolamine and/or heterocyclic amine compound represented by the following general formula (2) (hereinafter, to be referred to as a heterocyclic amine compound (2)).

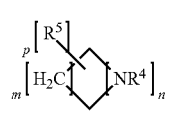

(2)

In the above-described formula (2), $R^4$ indicates a hydrogen atom or a substituted or non-substituted alkyl group having 1 to 4 carbon atoms. $R^5$ indicates a substituted or non-substituted alkyl group having 1 to 4 carbon atoms substituting a hydrogen atom which is coupled to a carbon atom. "n" indicates an integer number of 1 to 3, "m" indicates an integer number of 1 to 4, and "p" indicates an integer number of 0 to 12. When "n" is 2 or 3, nitrogen atoms are not directly coupled with each other.

In this embodiment, it is possible to mix, for example, the secondary amine compound (1) and the reaction accelerator composed of the alkanolamine and/or the heterocyclic amine compound (2). Then, it is possible to use the one in which the mixture of these is made into, for example, a water solution as the acid gas absorbent.

By using the secondary amine compound (1) mixed with the alkanolamine and/or the heterocyclic amine compound (2), it is possible to further improve the carbon dioxide absorption amount per unit mol of the secondary amine compound (1), the carbon dioxide absorption amount per unit volume of the acid gas absorbent and the carbon dioxide absorption speed.

Further, the use of the secondary amine compound (1) mixed with the alkanolamine and/or the heterocyclic amine compound (2) lowers energy to separate the acid gas after the absorption of carbon dioxide (acid gas desorption energy), and also makes it possible to decrease energy required when the acid gas absorbent is regenerated.

As alkanolamine, there can be cited, for example, monoethanolamine, 2-amino-2-methyl-1-propanol, 2-amino-2-methyl-1,3-propanediol, methylaminoethanol, diethanolamine, bis(2-hydroxy-1-methylethyl)amine, methyldiethanolamine, dimethylethanolamine, diethylethanolamine, triethanolamine, dimethylamino-1-methylethanol, 2-methylaminoethanol, 2-(ethylamino)ethanol, 2-propylaminoethanol, n-butylaminoethanol, 2-(isopropylamino)ethanol, 3-ethylaminopropanol, and so on.

Among the above, the alkanolamine is preferably at least one selected from the group consisting of 2-(isopropylamino)ethanol, 2-(ethylamino)ethanol, and 2-amino-2-methyl-1-propanol, from the viewpoint of improving the reactivity of the secondary amine compound (1) and the acid gas.

As the heterocyclic amine compound (2), there can be cited, azetidine, 1-methylazetidine, 1-ethylazetidine, 2-methylazetidine, 2-azetidylmethanol, 2-(2-aminoethyl) azetidine, pyrrolidine, 1-methylpyrrolidine, 2-methylpyrrolidine, 2-butylpyrrolidine, 2-pyrrolidylmethanol, 2-(2-aminoethyl)pyrrolidine, piperidine, 1-methylpiperidine, 2-ethylpiperidine, 3-propylpiperidine, 4-ethylpiperidine, 2-piperidylmethanol, 3-piperidylethanol, 2-(2-aminoethyl) pyrrolidine, hexahydro-1H-azepine, hexamethylenetetramine, piperazine compound (including piperazine and piperazine derivatives), and so on.

Among them, the piperazine compound is particularly desirable from the viewpoint of improving the carbon dioxide absorption amount and the absorption speed of the acid gas absorbent. The piperazine compound is the secondary amine compound. In general, the nitrogen atom of the secondary amino group is coupled to carbon dioxide to form a carbamate ion, and thereby, it contributes to the improvement of the absorption speed at an initial stage of the reaction. Further, the nitrogen atom of the secondary amino group has a role of converting the carbon dioxide coupled thereto into a bicarbonate ion ($HCO_3^-$), and contributes to the improvement of the speed at a latter half stage of the reaction.

The piperazine compound is more preferably at least one selected from the group consisting of piperazine, 2-methylpiperazine, 2,5-dimethylpiperazine, and 2,6-dimethylpiperazine.

A content of the reaction accelerator (the alkanolamine and/or the heterocyclic amine compound (2)) contained in the acid gas absorbent is preferably 1 mass % to 20 mass %. There is a possibility that the effect of improving the carbon dioxide absorption speed cannot be fully obtained when the content of the reaction accelerator contained in the acid gas absorbent is less than 1 mass %. When the content of the reaction accelerator contained in the acid gas absorbent exceeds 20 mass %, there is a possibility that the reactivity conversely decreases because the viscosity of the absorbent becomes excessively high. The content of the reaction accelerator (the alkanolamine and/or the heterocyclic amine compound (2)) is more preferably 5 mass % to 15 mass %.

The acid gas absorbent may contain an anticorrosive of a phosphoric acid based material or the like to prevent corrosion of plant equipment, a defoamer of a silicone based material or the like to prevent effervescence, an antioxidant to prevent deterioration of the acid gas absorbent, and so on, in addition to the secondary amine compound (1) and the reaction accelerator described above.

An acid gas removal method according to this embodiment includes bringing gas containing acid gas into contact with the acid gas absorbent according to the above-described embodiment, and thereby absorbing and separating the acid gas from the gas to remove it. In an acid gas removal method according to this embodiment, for example exhaust gas containing acid gas is brought into contact with an acid gas absorbent made by dissolving the secondary amine compound (1) described in the above embodiment in a solvent, and thereby the acid gas is absorbed and separated from the exhaust gas containing the acid gas to be removed.

An absorption and separation process of the acid gas, for example, carbon dioxide includes: a carbon dioxide absorption process; and a carbon dioxide separation process. In the carbon dioxide absorption process, exhaust gas containing carbon dioxide is brought into contact with an acid gas absorbent, to thereby make the acid gas absorbent absorb the carbon dioxide. In the carbon dioxide separation process, the acid gas absorbent that has absorbed the carbon dioxide in the above-described carbon dioxide absorption process is heated, to thereby desorb and recover the carbon dioxide.

In the carbon dioxide absorption process, the method of bringing the gas containing the carbon dioxide into contact with the above-described acid gas absorbent is not particularly limited. In the carbon dioxide absorption process, for example, a method in which the gas containing the carbon dioxide is bubbled in the acid gas absorbent, and thereby the carbon dioxide is absorbed, a method in which the acid gas absorbent is atomized and sprayed in a flow of the gas containing the carbon dioxide (atomizing and spraying method), a method in which the gas containing the carbon dioxide is brought into countercurrent contact with the acid gas absorbent in an absorption tower containing a filler made of a porcelain or a filler made of a metal net, or the like is performed.

In the carbon dioxide absorption process, a temperature of the acid gas absorbent when the gas containing the carbon dioxide is brought into contact with the acid gas absorbent and the carbon dioxide is absorbed is preferably from a room temperature to 60° C. or less. The temperature is more preferably 50° C. or less and particularly preferably approximately 20° C. to 45° C., where the carbon dioxide absorption process is performed. The absorption amount of the acid gas increases as the carbon dioxide absorption process is performed at a lower temperature, but a lower limit value of the process temperature is determined by a gas temperature, a heat recovery target and so on in the process. A pressure at the carbon dioxide absorption is normally approximately the atmospheric pressure. It is also possible to pressurize up to higher pressure to increase the absorption performance, but in order to suppress energy consumption required for compression, the carbon dioxide absorption is preferably performed under the atmospheric pressure.

In the carbon dioxide absorption process, the carbon dioxide absorption amount at the time when the carbon dioxide is absorbed (40° C.) by the acid gas absorbent containing 10 mass % to 55 mass % of the secondary amine compound (1) according to the above-described embodiment is approximately 0.26 mol to 0.62 mol per 1 mol of the secondary amine compound (1) contained in the absorbent. Further, the carbon dioxide absorption speed after a few minutes since the start of the absorption of the carbon dioxide is approximately 0.029 mol/mol/min to 0.038 mol/mol/min.

Here, a carbon dioxide saturation absorption amount is a value of an inorganic carbon amount in the acid gas absorbent measured by an infrared gas concentration measurement device. Further, the carbon dioxide absorption speed is a value measured by using an infrared carbon dioxide sensor at a time after a few minutes since the start of the absorption of the carbon dioxide.

In the carbon dioxide separation process, as a method of separating the carbon dioxide from the acid gas absorbent that has absorbed the carbon dioxide, and recovering pure or high-concentration carbon dioxide, there can be cited, a method of desorbing the carbon dioxide by heating the acid gas absorbent and beating it in a pot similar to distillation, a method of spreading a liquid interface in a plate tower, a spray tower, and a regeneration tower containing a filler made of a porcelain or a filler made of a metal net, followed by heating, and so on. The carbon dioxide is thereby isolated and released from carbamate anion and bicarbonate ion.

In the carbon dioxide separation process, a temperature of the acid gas absorbent when the carbon dioxide is separated is normally 70° C. or more. The temperature of the acid gas absorbent when the carbon dioxide is separated is preferably 80° C. or more, and more preferably approximately 90° C. to 120° C. The absorption amount increases as the temperature is higher, but energy required for the heating of the acid gas absorbent increases if the temperature is increased. Therefore, the temperature of the acid gas absorbent at the carbon dioxide separation time is determined by the gas temperature, the heat recovery target, and so on in the process. An absolute pressure at the carbon dioxide desorption is normally approximately 0.5 MPa to 5 MPa and preferably approximately 1 MPa to 4 MPa.

The carbon dioxide desorption amount of the acid gas absorbent containing 10 mass % to 55 mass % of the secondary amine compound (1) according to the above-described embodiment at the carbon dioxide desorption (80° C.) is approximately 0.15 mol to 0.47 mol per 1 mol of the secondary amine compound (1) contained in the absorbent.

The acid gas absorbent after the carbon dioxide is separated is transferred to the carbon dioxide absorption process again and is cyclically used (recycled). Further, the heat generated when the carbon dioxide is absorbed is generally heat exchanged by a heat exchanger for preheating the acid gas absorbent to be injected into the regeneration tower during a recycle process of the acid gas absorbent, and is cooled.

The purity of the carbon dioxide recovered as above is normally extremely high, which is approximately 95 vol % to 99 vol %. This pure carbon dioxide or high-concentration carbon dioxide is used as chemicals, synthetic raw materials of polymer, a coolant for freezing foods, and so on. In addition, it is also possible to isolate and store the recovered carbon dioxide in an underground or the like that is currently technically developed.

Among the above-described processes, the process of separating the carbon dioxide from the acid gas absorbent and regenerating the acid gas absorbent (carbon dioxide separation process) consumes the largest amount of energy. In this carbon dioxide separation process, approximately 50% to 80% of the energy consumed in all the processes is consumed. Thus, by decreasing the consumption energy in the carbon dioxide separation process in which the acid gas absorbent is regenerated, the cost of the absorption and separation processes of the carbon dioxide can be decreased. Thereby, it is possible to remove the acid gas from the exhaust gas advantageously from an economical viewpoint.

According to this embodiment, it is possible to decrease the energy required for the carbon dioxide separation process (regeneration process) by using the acid gas absorbent in the above-described embodiment. Therefore, it is possible to perform the absorption and separation processes of the carbon dioxide under an economically advantageous condition.

Further, the secondary amine compound (1) according to the above-described embodiment has extremely high corrosion-resistance to a metal material such as a carbon steel, compared to alkanolamine such as monoethanolamine that have been conventionally used as the acid gas absorbent. Thus, it is cost-advantageous to use the acid gas removal method using the acid gas absorbent in this embodiment because it is not necessary to use expensive high-grade corrosion-resistant steel in, for example, plant construction.

An acid gas removal device according to this embodiment being an acid gas removal device that removes acid gas from gas containing the acid gas, includes: an absorption tower housing the acid gas absorbent according to the above-described embodiment therein and bringing the gas containing the acid gas into contact with the acid gas absorbent to remove the acid gas from the gas; and a regeneration tower housing the acid gas absorbent containing the acid gas absorbed in the absorption tower therein and removing the acid gas from the acid gas absorbent to regenerate the acid gas absorbent to be reused in the absorption tower.

FIG. 1 is a schematic diagram of the acid gas removal device according to an embodiment. This acid gas removal device 1 includes: an absorption tower 2; and a regeneration tower 3. In the acid gas removal device 1, the absorption tower 2 brings gas containing acid gas (hereinafter, to be referred to as exhaust gas) into contact with an acid gas absorbent to absorb and remove the acid gas from the exhaust gas. In the acid gas removal device 1, the regeneration tower 3 separates the acid gas from the acid gas absorbent that has absorbed the acid gas in the absorption tower 2 to regenerate the acid gas absorbent. Hereinafter, the case when the acid gas is carbon dioxide will be explained as an example.

As illustrated in FIG. 1, exhaust gas containing carbon dioxide, such as exhaust combustion gas to be discharged from a thermal power station, is introduced into a lower part of the absorption tower 2 through a gas supply port 4. An acid gas absorbent is supplied from an acid gas absorbent supply port 5 at an upper part of the absorption tower 2 to be housed in the absorption tower 2. The exhaust gas introduced into the absorption tower 2 is brought into contact with the acid gas absorbent housed in the absorption tower 2. The acid gas absorbent according to the above-described embodiment is used as the acid gas absorbent.

A pH value of the acid gas absorbent is preferably adjusted to at least 9 or more. An optimum condition of the pH value of the acid gas absorbent is preferably selected as necessary depending on a kind, concentration, a flow rate, or the like of harmful gas contained in the exhaust gas. Further, the acid gas absorbent may also contain other compounds such as a nitrogen-containing compound improving the absorption performance of carbon dioxide, an antioxidant, and a pH adjusting agent in arbitrary ratios, in addition to the above-described secondary amine compound (1), reaction accelerator, and the solvent such as water.

As stated above, the exhaust gas is brought into contact with the acid gas absorbent in the absorption tower 2, and thereby the carbon dioxide in the exhaust gas is absorbed by the acid gas absorbent to be removed from the exhaust gas. The exhaust gas after the carbon dioxide is removed is discharged to the outside of the absorption tower 2 from a gas discharge port 6.

The acid gas absorbent that has absorbed the carbon dioxide is transferred to a heat exchanger 7 and a heater 8 sequentially from the absorption tower 2 to be heated, and thereafter, transferred to the regeneration tower 3. The acid gas absorbent transferred into the regeneration tower 3 is moved from an upper part to a lower part of the regeneration tower 3, and during the moving, the carbon dioxide in the acid gas absorbent is desorbed, and the acid gas absorbent is regenerated.

The acid gas absorbent regenerated in the regeneration tower 3 is transferred to the heat exchanger 7 and an absorbing liquid cooler 10 sequentially by a pump 9, and is returned to the absorption tower 2 through the acid gas absorbent supply port 5.

On the other hand, the carbon dioxide separated from the acid gas absorbent is brought into contact with reflux water supplied from a reflux drum 11 at the upper part of the regeneration tower 3 to be discharged to the outside of the regeneration tower 3. The reflux water in which the carbon dioxide is dissolved is cooled in a reflux condenser 12, and thereafter, in the reflux drum 11, the reflux water is separated from a liquid component in which vapor with the carbon dioxide is condensed. This liquid component is introduced into the carbon dioxide recovery process by a recovery carbon dioxide line 13. On the other hand, the reflux water from which the carbon dioxide is separated is transferred to the regeneration tower 3 by a reflux water pump 14.

According to the acid gas removal device 1 in this embodiment, it becomes possible to absorb and remove carbon dioxide with high efficiency by using the acid gas absorbent excellent in carbon dioxide absorption property and desorption property.

EXAMPLES

Hereinafter, the present invention will be explained in more detail with reference to examples and comparative examples. Incidentally, the present invention is not limited to these examples.

Example 1

A 50 ml water solution (hereinafter, to be referred to as an absorbing liquid) was prepared by dissolving 2-[2-(cyclopentylamino)ethoxy]ethanol as the secondary amine compound (1) and piperazine as the reaction accelerator in water so that the contents of them become 45 mass % and 5 mass % respectively to total mass of the absorbing liquid. This absorbing liquid was filled in a test tube and heated to 40° C., and then a mixed gas containing 10 vol % of carbon dioxide ($CO_2$) and 90 vol % of nitrogen ($N_2$) gas was aerated in the absorbing liquid at a flow rate of 400 mL/min. Then, absorption performance was evaluated by measuring the carbon dioxide ($CO_2$) concentration in the gas to be discharged from an exit of the test tube by using an infrared gas concentration measurement device (manufactured by SHIMADZU CORPORATION, product name "CGT-700").

The absorbing liquid in which the mixed gas was absorbed at 40° C. as described above was heated to 80° C., 100% nitrogen ($N_2$) gas was aerated at a flow rate of 500 mL/min, and the $CO_2$ concentration in the absorbing liquid was measured by using the infrared gas concentration measurement device to evaluate a release performance.

A carbon dioxide absorption speed of the absorbing liquid was set to the speed measured at a time after two minutes since the start of the absorption of carbon dioxide.

Heat of reaction was measured as follows. A differential reaction calorimeter "DRC Evolution" (product name, manufactured by SETARAM) made up of a glass reaction vessel and a reference vessel with the same shape installed in a thermostatic oven was used to measure the heat of reaction of the carbon dioxide absorption by the absorbing liquid. The reaction vessel and the reference vessel were each filled with 150 mL of the absorbing liquid, and constant-temperature water at 40° C. was circulated in jacket portions of the vessels. In this state, carbon dioxide gas with a 100% concentration was blown to the absorbing liquid in the reaction vessel at 200 ml/min, and a temperature increase of the absorbing liquid was continuously recorded by a thermograph until the carbon dioxide absorption was finished. Then, the heat of reaction was calculated by using an overall heat transfer coefficient between the reaction vessel and the jacket water that was measured in advance.

Diffusion performance of the secondary amine compound (1) was evaluated as follows. Namely, the absorbing liquid was supplied into a flask with a cooling tube attached thereto, and thereafter, the flask and all was heated to 120° C. During this period, nitrogen gas was aerated in the absorbing liquid at a rate of 100 ml/min. Then, a gas component diffused from the cooling tube was recovered, and an amount of the secondary amine compound (1) contained in the recovered gas was measured. (diffusion performance test)

A carbon dioxide ($CO_2$) absorption amount of the absorbing liquid at 40° C. was 0.52 mol per 1 mol of the secondary amine compound (1) in the absorbing liquid. A carbon dioxide ($CO_2$) absorption amount of the absorbing liquid at 80° C. was 0.24 mol per 1 mol of the secondary amine compound (1). In a process of absorbing the carbon dioxide ($CO_2$) at 40° C. and desorbing the carbon dioxide ($CO_2$) at 80° C., 0.28 mol of $CO_2$ was recovered per 1 mol of the secondary amine compound (1). A carbon dioxide absorption speed was 0.0065 mol/mol/min.

Example 2

An absorbing liquid was prepared in the same manner as in EXAMPLE 1 except that 2-[2-(cyclohexylamino)ethoxy]ethanol was used in place of 2-[2-(cyclopentylamino)ethoxy]ethanol. Then, a carbon dioxide absorption amount, a carbon dioxide absorption speed, heat of reaction, and a recovery amount of the secondary amine compound (1) were measured under the same conditions by using the same devices as those of EXAMPLE 1.

The carbon dioxide absorption amount at 40° C. was 0.46 mol and the carbon dioxide absorption amount at 80° C. was 0.23 mol, per 1 mol of the secondary amine compound (1) in the absorbing liquid. Then, 0.23 mol of carbon dioxide was recovered per 1 mol of the secondary amine compound (1) in the absorbing liquid. The carbon dioxide absorption speed was 0.0055 mol/mol/min.

Example 3

An absorbing liquid was prepared in the same manner as in EXAMPLE 1 except that a compounding amount of 2-[2-(cyclopentylamino)ethoxy]ethanol was set to be 55 mass %. Then, a carbon dioxide absorption amount, a carbon dioxide absorption speed, heat of reaction, and a recovery amount of the secondary amine compound (1) were measured under the same conditions by using the same devices as those of EXAMPLE 1.

The carbon dioxide absorption amount at 40° C. was 0.53 mol and the carbon dioxide absorption amount at 80° C. was 0.25 mol, per 1 mol of the secondary amine compound (1) in the absorbing liquid. Then, 0.28 mol of carbon dioxide was recovered per 1 mol of the secondary amine compound (1) in the absorbing liquid. The carbon dioxide absorption speed was 0.0064 mol/mol/min.

Example 4

An absorbing liquid was prepared in the same manner as in EXAMPLE 1 except that a compounding amount of 2-[2-(cyclopentylamino)ethoxy]ethanol was set to be 10 mass %. Then, a carbon dioxide absorption amount, a carbon dioxide absorption speed, heat of reaction, and a recovery amount of the secondary amine compound (1) were measured under the same conditions by using the same devices as those of EXAMPLE 1.

The carbon dioxide absorption amount at 40° C. was 0.30 mol and the carbon dioxide absorption amount at 80° C. was 0.08 mol, per 1 mol of the secondary amine compound (1) in the absorbing liquid. Then, 0.22 mol of carbon dioxide was recovered per 1 mol of the secondary amine compound (1) in the absorbing liquid. The carbon dioxide absorption speed was 0.0050 mol/mol/min.

Example 5

An absorbing liquid was prepared in the same manner as in EXAMPLE 1 except that 2-amino-2-methyl-1-propanol was used in place of piperazine. Then, a carbon dioxide absorption amount, a carbon dioxide absorption speed, heat of reaction, and a recovery amount of the secondary amine compound (1) were measured under the same conditions by using the same devices as those of EXAMPLE 1.

The carbon dioxide absorption amount at 40° C. was 0.53 mol and the carbon dioxide absorption amount at 80° C. was 0.25 mol, per 1 mol of the secondary amine compound (1) in the absorbing liquid. Then, 0.28 mol of carbon dioxide was recovered per 1 mol of the secondary amine compound (1) in the absorbing liquid. The carbon dioxide absorption speed was 0.0060 mol/mol/min.

Example 6

An absorbing liquid was prepared in the same manner as in EXAMPLE 1 except that 3-[2-(cyclopentylamino)ethoxy]-1-propanol was used in place of 2-[2-(cyclopentylamino)ethoxy]ethanol. Then, a carbon dioxide absorption amount, a carbon dioxide absorption speed, heat of reaction, and a recovery amount of the secondary amine compound (1) were measured under the same conditions by using the same devices as those of EXAMPLE 1.

The carbon dioxide absorption amount at 40° C. was 0.46 mol and the carbon dioxide absorption amount at 80° C. was 0.25 mol, per 1 mol of the secondary amine compound (1) in the absorbing liquid. Then, 0.21 mol of carbon dioxide was recovered per 1 mol of the secondary amine compound (1) in the absorbing liquid. The carbon dioxide absorption speed was 0.0050 mol/mol/min.

Example 7

An absorbing liquid was prepared in the same manner as in EXAMPLE 1 except that 4-[2-(cyclopentylamino)ethoxy]-1-butanol was used in place of 2-[2-(cyclopentylamino)ethoxy]ethanol. Then, a carbon dioxide absorption amount, a carbon dioxide absorption speed, heat of reaction, and a recovery amount of the secondary amine compound (1) were measured under the same conditions by using the same devices as those of EXAMPLE 1.

The carbon dioxide absorption amount at 40° C. was 0.40 mol and the carbon dioxide absorption amount at 80° C. was 0.25 mol, per 1 mol of the secondary amine compound (1) in the absorbing liquid. Then, 0.15 mol of carbon dioxide was recovered per 1 mol of the secondary amine compound (1) in the absorbing liquid. The carbon dioxide absorption speed was 0.0048 mol/mol/min.

Comparative Example 1

A 50 ml water solution (hereinafter, to be referred to as an absorbing liquid) was prepared by dissolving N-butyl-N-methylethanolamine (hereinafter, to be referred to as an amine compound (cf1)) and piperazine in water so that the contents of them become 60 mass % and 5 mass % respectively to total mass of the absorbing liquid. Then, a carbon dioxide absorption amount, a carbon dioxide absorption speed, heat of reaction, and a recovery amount of the amine compound (cf1) were measured under the same conditions as EXAMPLE 1 by using the same devices as those of EXAMPLE 1.

The carbon dioxide absorption amount at 40° C. was 0.38 mol and the carbon dioxide absorption amount at 80° C. was 0.12 mol, per 1 mol of the amine compound (cf1) in the absorbing liquid. Then, 0.26 mol of carbon dioxide was recovered per 1 mol of the amine compound (cf1) in the absorbing liquid. The carbon dioxide absorption speed was 0.0040 mol/mol/min.

Comparative Example 2

An absorbing liquid was prepared in the same manner as in EXAMPLE 1 except that 2-[2-(cyclobutylamino)ethoxy]ethanol (hereinafter, to be referred to as an amine compound (cf2)) was used in place of 2-[2-(cyclopentylamino)ethoxy]ethanol. Then, a carbon dioxide absorption amount, a carbon dioxide absorption speed, heat of reaction, and a recovery amount of the amine compound (cf2) were measured under the same conditions by using the same devices as those of EXAMPLE 1.

The carbon dioxide absorption amount at 40° C. was 0.53 mol and the carbon dioxide absorption amount at 80° C. was 0.30 mol, per 1 mol of the amine compound (cf2) in the absorbing liquid. Then, 0.23 mol of carbon dioxide was recovered per 1 mol of the amine compound (cf2) in the absorbing liquid. The carbon dioxide absorption speed was 0.0065 mol/mol/min.

Comparative Example 3

An absorbing liquid was prepared in the same manner as in EXAMPLE 1 except that 2-[2-(cycloheptylamino)ethoxy]ethanol (hereinafter, to be referred to as an amine compound (cf3)) was used in place of 2-[2-(cyclopentylamino)ethoxy]ethanol. Then, a carbon dioxide absorption amount, a carbon dioxide absorption speed, heat of reaction, and a recovery amount of the amine compound (cf3) were measured under the same conditions by using the same devices as those of EXAMPLE 1.

The carbon dioxide absorption amount at 40° C. was 0.35 mol and the carbon dioxide absorption amount at 80° C. was 0.20 mol, per 1 mol of the amine compound (cf3) in the absorbing liquid. Then, 0.15 mol of carbon dioxide was recovered per 1 mol of the amine compound (cf3) in the absorbing liquid. The carbon dioxide absorption speed was 0.0035 mol/mol/min.

The measurement results of the carbon dioxide absorption amount at 40° C., the carbon dioxide absorption amount at 80° C., the carbon dioxide recovery amount, the carbon dioxide absorption speed, the heat of reaction, and the recovery amount of each amine compound in the diffusion performance test in EXAMPLES 1 to 7 and COMPARATIVE EXAMPLES 1 to 3 are illustrated in Table 1, together with the contents of each amine compound and the reaction accelerator in the absorbing liquid. Note that in Table 1, the carbon dioxide absorption amount and the carbon dioxide recovery amount are the absorption amount and the recovery amount per 1 mol of each amine compound contained in the absorbing liquid, which are expressed in the number of moles.

TABLE 1

| | | | E1 | E2 | E3 | E4 | E5 | E6 | E7 | CE1 | CE2 | CE3 |
|---|---|---|---|---|---|---|---|---|---|---|---|---|
| Contents in absorbing liquid [mass %] | Secondary amine compound (1) | 2-[2-(Cyclopentylamino) Ethoxy] Ethanol | 45 | — | 55 | 10 | 45 | — | — | — | — | — |
| | | 2-[2-(Cyclohexylamino) Ethoxy] Ethanol | — | 45 | — | — | — | — | — | — | — | — |
| | | 3-[2-(Cyclopentylamino) Ethoxy]-1-Propanol | — | — | — | — | — | 45 | — | — | — | — |
| | | 4-[2-(Cyclopentylamino) Ethoxy]-1-Butanol | — | — | — | — | — | — | 45 | — | — | — |
| | Other amine compounds | | — | — | — | — | — | — | — | 60 | 45 | 45 |
| | Reaction Accelerator | Alkanolamine | — | — | — | — | 5 | — | — | — | — | — |
| | | Heterocyclic amine compound (2) | 5 | 5 | 5 | 5 | — | 5 | 5 | 5 | 5 | 5 |
| $CO_2$ ABSORPTION AMOUNT (40° C.) [mol] | | | 0.52 | 0.46 | 0.53 | 0.30 | 0.53 | 0.46 | 0.40 | 0.38 | 0.53 | 0.35 |
| $CO_2$ ABSORPTION AMOUNT (80° C.) [mol] | | | 0.24 | 0.23 | 0.25 | 0.08 | 0.25 | 0.25 | 0.25 | 0.12 | 0.30 | 0.20 |
| $CO_2$ RECOVERY AMOUNT [mol] | | | 0.28 | 0.23 | 0.28 | 0.22 | 0.28 | 0.21 | 0.15 | 0.26 | 0.23 | 0.15 |
| $CO_2$ ABSORPTION SPEED [mol/mol/min] | | | 0.0065 | 0.0055 | 0.0064 | 0.0050 | 0.0060 | 0.0050 | 0.0048 | 0.0040 | 0.0065 | 0.0035 |
| HEAT OF REACTION [kJ/mol] | | | 72 | 73 | 72 | 73 | 74 | 73 | 73 | 76 | 76 | 73 |
| DIFFUSION PERFORMANCE [MASS %] | | | 0.0 | 0.0 | 0.0 | 0.0 | 0.0 | 0.0 | 0.0 | 1.0 | 0.0 | 0.0 |

E1 to E7 = Example 1 to Example 7: CE 1 to CE 3 = Comparative Example 1 to Comparative Example 3

As it is obvious from Table 1, in the absorbing liquids of EXAMPLES 1 to 7 each using the secondary amine compound (1) having a cyclopentyl group or a cyclohexyl group, the carbon dioxide absorption amount and the carbon dioxide recovery amount were both high, besides, the heat of reaction at the carbon dioxide absorption was low and the absorption performance of carbon dioxide was excellent. On the other hand, in the absorbing liquid of COMPARATIVE EXAMPLE 3 using the secondary amine compound having the cycloheptyl group, the heat of reaction was small, but the carbon dioxide absorption amount and the carbon dioxide recovery amount were low.

Besides, in the absorbing liquids of EXAMPLES 1 to 7 each using the secondary amine compound (1) having the cyclopentyl group or the cyclohexyl group, and in which the hydroxyl group is coupled to the nitrogen atom via the ether bond, the amine compound diffused from the absorbing liquid was seldom recognized in the diffusion performance test. On the other hand, in the absorbing liquid of COMPARATIVE EXAMPLE 1 using the tertiary amine compound not having the ether bond, the amine compound of approximately 1 mass % was recovered in the diffusion performance test.

According to the acid gas absorbent, the acid gas removal method, and the acid gas removal device of at least one of the embodiments described above, it is possible to increase the absorption amount of acid gas such as carbon dioxide, and to decrease the heat of reaction at the acid gas absorption.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An acid gas absorbent comprising 45 mass % to 55 mass % of at least one secondary amine compound represented by general formula (1),

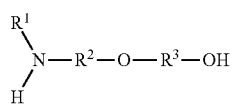

(1)

where $R^1$ indicates a cyclopentyl group which may be substituted by a substituted or non-substituted alkyl group having 1 to 3 carbon atoms, $R^2$ and $R^3$, which may be the same or different, each indicate an alkylene group having 2 to 4 carbon atoms and are a straight chain or have a side chain.

2. The acid gas absorbent according to claim 1, wherein, in the secondary amine compound represented by the general formula (1), $R^2$ and $R^3$ each independently indicate an alkylene group having 2 or 3 carbon atoms.

3. The acid gas absorbent according to claim 1, further comprising water.

4. The acid gas absorbent according to claim 1, comprising water and 45 mass % to 55 mass % of 2-[2-(cyclopentylamino)ethoxy]ethanol.

5. The acid gas absorbent according to claim 1, comprising water and 45 mass % to 55 mass % of 3-[2-(cyclopentylamino)ethoxy]-1-propanol.

6. The acid gas absorbent according to claim 1, comprising water and 45 mass % to 55 mass % of 4-[2-(cyclopentylamino)ethoxy]-1-butanol.

7. The acid gas absorbent according to claim 1, wherein the at least one secondary amine compound represented by general formula (1) is selected from 2-[2-(cyclopentylamino)ethoxy]ethanol, 2-[3-(cyclopentylamino)propoxy]ethanol, 2-[4-(cyclopentylamino)butoxy]ethanol, 3-[2-(cyclopentylamino)ethoxy]-1-propanol, 3-[3-(cyclopentylamino)propoxy]-1-propanol, 3-[4-(cyclopentylamino)butoxy]-1-propanol, 1-[2-(cyclopentylamino)ethoxy]-2-propanol, 1-[3-(cyclopentylamino)propoxy]-2-propanol, 1-[4-(cyclopentylamino)butoxy]-2-propanol, 4-[2-(cyclopentylamino)ethoxy]-1-butanol, 4-[3-(cyclopentylamino)propoxy]-1-butanol, and 4-[4-(cyclopentylamino)butoxy]-1-butanol.

8. The acid gas absorbent according to claim 1, further comprising 1 mass % to 20 mass % of an alkanolamine and/or a heterocyclic amine compound

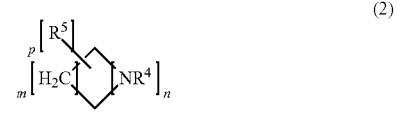

(2)

9. The acid gas absorbent according to claim 8, comprising an alkanolamine which is at least one selected from the group consisting of 2-(isopropylamino)ethanol, 2-(ethylamino)ethanol, and 2-amino-2-methyl-1-propanol.

10. The acid gas absorbent according to claim 8, comprising at least one kind of piperazine compound.

11. The acid gas absorbent according to claim 10, wherein the piperazine compound is at least one selected from the group consisting of piperazine, 2-methylpiperazine, 2,5-dimethylpiperazine, and 2,6-dimethylpiperazine.

12. The acid gas absorbent according to claim 8, wherein the alkanolamine and/or heterocyclic amine compound are selected from monoethanolamine, 2-amino-2-methyl-1-propanol, 2-amino-2-methyl-1,3-propanediol, methylaminoethanol, diethanolamine, bis(2-hydroxy-1-methylethyl) amine, methyldiethanolamine, dimethylethanolamine, diethylethanolamine, triethanolamine, dimethylamino-1-methylethanol, 2-methylaminoethanol, 2-(ethylamino)ethanol, 2-propylaminoethanol, n-butylaminoethanol, 2-(isopropylamino)ethanol, 3-ethylaminopropanol, azetidine, 1-methylazetidine, 1-ethylazetidine, 2-methylazetidine, 2-azetidylmethanol, 2-(2-aminoethyl)azetidine, pyrrolidine, 1-methylpyrrolidine, 2-methylpyrrolidine, 2-butylpyrrolidine, 2-pyrrolidylmethanol, 2-(2-aminoethyl)pyrrolidine, piperidine, 1-methylpiperidine, 2-ethylpiperidine, 3-propylpiperidine, 4-ethylpiperidine, 2-piperidylmethanol, 3-piperidylethanol, 2-(2-aminoethyl)pyrrolidine, hexahydro-1H-azepine, hexamethylenetetramine, piperazine, 2-methylpiperazine, 2,5-dimethyl piperazine, and 2,6-dimethylpiperazine.

13. An acid gas removal method comprising:
bringing gas containing acid gas into contact with the acid gas absorbent according to claim 1 to thereby remove the acid gas from the gas containing the acid gas.

14. The acid gas removal method according to claim 13, wherein the acid gas is carbon dioxide.

* * * * *